(12) United States Patent
Shershukov et al.

(10) Patent No.: US 6,288,232 B2
(45) Date of Patent: Sep. 11, 2001

(54) SYNTHESIS OF PYRAZOLINYLNAPHTHALIC ACID DERIVATIVES

(75) Inventors: Victor M. Shershukov; Valentina T. Skripkina, both of Kharkov (UA)

(73) Assignee: eMagin Corporation, Hopewell Junction, NY (US)

( * ) Notice: Subject to any disclaimer, the term of this patent is extended or adjusted under 35 U.S.C. 154(b) by 0 days.

(21) Appl. No.: 09/740,983

(22) Filed: Dec. 21, 2000

(30) Foreign Application Priority Data

Dec. 28, 1999 (UA) .................................. 99127167

(51) Int. Cl.$^7$ ...................... C07D 471/02; C07D 221/06
(52) U.S. Cl. ..................... 546/52; 546/98; 546/110
(58) Field of Search ................... 546/52, 98, 110

(56) References Cited

U.S. PATENT DOCUMENTS

| | | | |
|---|---|---|---|
| 3,718,652 | * | 2/1973 | Sureau et al. ............ 260/282 |
| 3,819,632 | * | 6/1974 | Burdeska et al. .......... 260/282 |
| 4,097,450 | * | 6/1978 | Papenfuhs et al. ........ 260/42.21 |
| 5,071,482 | * | 12/1991 | Dietz et al. ............. 106/498 |
| 5,071,483 | * | 12/1991 | Dietz et al. ............. 106/498 |
| 5,074,919 | * | 12/1991 | Dietz et al. ............. 106/494 |

OTHER PUBLICATIONS

B.M. Krasovitsky et al. Journal of Luminescence, vol. 8 No. 1 (1973), pp. 44–50.*

B.M. Krasovitsky et al USSR Authors Certificate (A.C.) #196873, c09d, B. I, 2 (1967).*

* cited by examiner

Primary Examiner—Deborah C. Lambkin
Assistant Examiner—Kamal Saeed
(74) Attorney, Agent, or Firm—John N. Coulby; Collier Shannon Scott, PLLC

(57) ABSTRACT

The invention pertains to a method for preparing derivatives of the pyrazolinylnaphthalic acid having the general formula

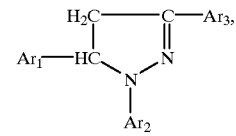

where $Ar_1$ and $Ar_2$ are unsubstituted or substituted phenyl radicals bearing in the para position an alkylated or acylated oxy- or amino group, or a polynuclear aryl radical, and $Ar_3$ is a substituted N-naphthalimid or 1,8-naphthylene-1',2'-benzimidazole. Compounds of the above general formula are high-efficient red organic luminophors and are used widely as luminescent components of dyes for plastics and liquid scintillators, in hydrogeology to study water streams, to label the chemical industry wastewaters, as laser dyes, etc.

45 Claims, No Drawings

SYNTHESIS OF PYRAZOLINYLNAPHTHALIC ACID DERIVATIVES

CROSS REFERENCE TO RELATED PATENT APPLICATIONS

This application is related to and claims priority on Ukrainian patent application serial number 99127167, filed Dec. 28, 1999.

FIELD OF THE INVENTION

The invention relates to a method for preparing derivatives of the pyrazolinylnaphthalic acid having the general formula

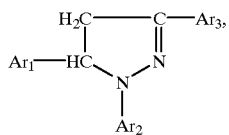

where

Ar$_1$ and Ar$_2$ are unsubstituted or substituted phenyl radicals bearing in the para position an alkylated or acylated oxy- or amino group, or a polynuclear aryl radical; and Ar$_3$ is a substituted N-naphthalimid or 1,8-naphthylene-1',2'-benzimidazole.

BACKGROUND OF THE INVENTION

A method is known (see Ref.1—USSR Author's Certificate No. 179,324, Cl. C09d) for preparing derivatives of pyrazolinylnaphthalic acid having the general formula

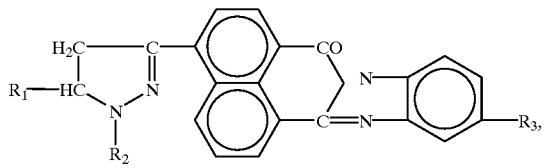

where

R$_1$ is a unsubstituted or substituted aromatic or heterocyclic radical;

R$_2$ is a unsubstituted or substituted aromatic radical;

R$_3$ is an alkyl, aryl, alkoxy, or halogen.

Compounds of this general formula are organic luminophors with emission in the orange-red and red range of the visible spectrum.

The above-mentioned compounds are prepared proceeding from condensation products of 4-acetylnaphthalic anhydride with unsubstituted or substituted o-phenylene diamine in glacial acetic acid. The yellowish green crystals formed are filtered off and recrystallized from acetic acid. The acetyl derivative of 1,8-naphthylene-1',2'-benzimidazole obtained is treated with aromatic or heterocyclic aldehyde in ethanol in the presence of sodium hydroxide, stirred at ambient temperature, and diluted with water. The precipitate formed is separated by filtration and recrystallized from acetic acid. An unsaturated ketone is obtained. The ketone is treated with phenyl hydrazine or its substitute in glacial acetic acid under reflux, the crystals precipitated from the cooled solution are filtered off, washed with methanol, and dried. The product is obtained as water-insoluble red or dark-red crystals soluble in conventional organic solvents. The ready (commercial grade) product yield is from 62 to 85%. Luminescence characteristics: in toluene, $\lambda_{max}$=598 to 610 nm; in crystal form, $\lambda_{max}$=620 to 670 nm.

Another method has been also described (see Ref.2—USSR Author's Certificate No. 196,873, Cl. C09d) for preparing derivatives of pyrazolinylnaphthalic acid having general formula

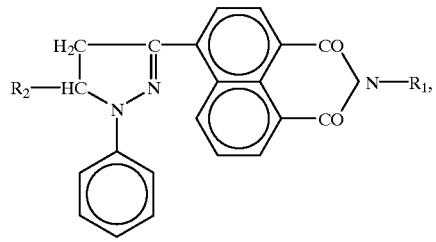

where

R$_1$ and R$_2$ are unsubstituted or substituted aromatic radicals. Compounds of this structure are organic luminophors with orange, orange-red, and red emission.

The method consists of a first synthesis stage, in which a mixture of 4-acetylnaphthalic anhydride, aniline, and glacial acetic acid is heated under reflux, the reaction mixture is cooled, the precipitated gray crystals are separated by filtration, treated with hydrochloric acid solution, then with hot sodium carbonate solution, and recrystallized from acetic acid. Acetyl derivative, the 4-acetylnaphthalic acid phenylimide is obtained.

At the second stage, the acetyl derivative, the 4-acetylnaphthalic acid phenylimide, is converted into an unsaturated ketone. To that end, 4-acetylnaphthalic acid phenylimide, ethanol, sodium hydroxide solution, and benzaldehyde are stirred at ambient temperature. The precipitate formed is separated by filtration, water washed till neutral reaction (litmus), dried, and re-crystallized from toluene. The product is obtained as yellow crystals.

At the third synthesis stage, the unsaturated ketone is treated with phenyl hydrazine in a mixture of ethanol and sodium hydroxide solution under reflux. The crystals precipitated from the mixture under cooling are separated by filtration, water washed till neutral reaction, and treated with boiling alcohol. The product obtained is purified using chromatography of toluene solution. The final product is obtained as red crystals at yield of 57 to 64%. The crystals are water-insoluble and soluble in organic solvents. Luminescence: in toluene, $\lambda_{max}$=570 nm.

The methods for preparing luminophors disclosed in the above-mentioned Author's Certificates are almost identical with each other except for that 4-acetylnaphthalic anhydride is treated with aniline to obtain orange-red luminophors (Ref.2) while to produce red ones, the same anhydride is reacted with o-phenylene diamine.

In this reaction, the same drawbacks are typical of both methods, namely:

(A) Low quality of the final product. The product contains considerable amounts of impurities, mainly unsaturated naphthalic acid derivatives that cause green fluorescence. The presence of such impurities in the final product is due to the preparation method itself. The final product purification from the impurities mentioned is associated with difficulties in the process, increased production costs, and substantial losses of the final product. To obtain high-quality luminophors, the chromatographic purification is required resulting in a loss of 30 to 40% of the final product. In Ref.2 the yields of various red range luminophors are said to be from 62 to 85%. The real useful product yield after the purification is, however, only from 35 to 50%.

(B) The process is difficult to perform and laborious. When producing orange, orange-red, and red luminophors, the corresponding intermediates, i.e., acetyl derivatives, are to be prepared every time. For example, 4-acetylnaphthalic anhydride is to be condensed with aniline preparing 4-acetylnaphthalic acid phenylimide to produce luminophors emitting in orange range, while to obtain red luminophors, the same anhydride must be condensed with o-phenylene diamine preparing 4(5)-acetyl-1,8-naphthoylene-1',2'-benzimidazole. These preparations make the process difficult and increase its cost.

(C) Moreover, the process is complicated by the purification of intermediates both at the stages of their synthesis and at the preparation of final products.

Another method is known for preparing luminophors of the structure and emission region similar to the subject of this application; the method consists in that 4-cinnamoyl-1, 8-naphthylene-1',2'-benzimidazole is condensed with o-tolyl hydrazine in acetic acid medium under boiling, i.e., similar to the methods described above. The precipitate formed is separated by filtration, dried, and purified by the column chromatography. By this method, 4-[1-(2-methylphenyl)-5-phenyl-2-pyrazolinyl-3]-1,8-naphthoylene-1',2'-benzimidazole with the structure shown is obtained.

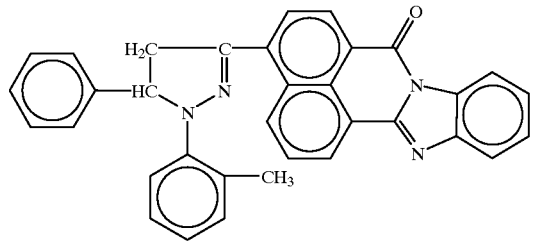

The luminophore compounds so prepared are fluorescent in the orange-red spectral region with a large Stokes shift: in toluene, absorption at $\lambda_{max}$=470 nm, luminescence at $\lambda_{max}$=595 nm. (See Ref.3—USSR Author's Certificate No. 1,148, 291, Cl. C09K 11/06).

The use of the method of the present invention will permit the synthesis of the named luminophores to be carried out faster with a higher yield of the product. That will eliminate the extra cost related to the use of chemicals and labor and will provide for the more economical synthesis of the product.

REFERENCES

1. B. M. Krasovitskiy and E. A. Shevchenko "Method of preparation of organic luminophores", USSR Authors Certificate (A.C.) #179324, c09d, B. I, 5 (1966).
2. B. M. Krasovitskiy, E. G. Yushko, and D. G. Pereyaslova "Method of preparation of organic luminophores", USSR Authors Certificate (A.C.) #196873, c09d, B. I, 2 (1967).
3. V. M. Shershukov, B. M. Krasovitskiy and T. A. Shehovtsova "4-[1-(2-methylphenyl)-5-phenyl-2-pirazolynil-3]-1',8'-naphthoylen-1',2'-benzimidazole as an orange-red luminophore", USSR Authors Certificate (A.C.) #1148291, c09k, 11/06, B. I, 47–48 (1993).

The USSR Authors Certificate is an equivalent of a patent that has been filed in the USSR only.

OBJECTS OF THE INVENTION

It is therefore an object of the present invention to develop a method for preparing pyrazolinylnaphthalic acid derivatives of the general formula

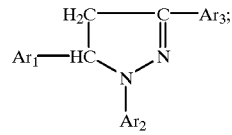

where

Ar$_1$ and Ar$_2$ are unsubstituted or substituted phenyl radicals bearing in the para position an alkylated or acylated oxy or amino group, or a polynuclear aryl radical; and Ar$_3$ is a substituted N-naphthalimid or 1,8-naphthylene-1',2'-benzimidazole.

It is another object of the present invention to provide a method to simplify and reduce the time it takes to synthesize the above compounds.

It is a further object of the present invention to enhance the final product yield and quality (purity grade) of the above compounds.

Additional objects and advantages of the invention are set forth, in part, in the description which follows and, in part, will be apparent to one of ordinary skill in the art from the description and/or from the practice of the invention.

SUMMARY OF THE INVENTION

In response to the foregoing challenge, Applicants have developed an innovative, economical method for preparing derivatives of the pyrazolinylnaphthalic acid having the general formula

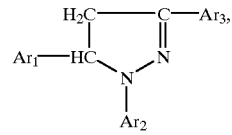

where

Ar$_1$ and Ar$_2$ are unsubstituted or substituted phenyl radicals bearing in the para position an alkylated or acylated oxy- or amino group, or a polynuclear aryl radical; and Ar$_3$ is a substituted N-naphthalimid or 1,8-naphthylene-1',2'-benzimidazole.

It is to be understood that both the foregoing general description and the following detailed description are exemplary and explanatory only, and are not restrictive of the invention as claimed. The accompanying drawings, which are incorporated herein by reference, and which constitute a part of this specification, illustrate certain embodiments of the invention, and together with the detailed description serve to explain the principles of the present invention.

DETAILED DESCRIPTION OF THE PREFERRED EMBODIMENTS

Reference will now be made in detail to a preferred embodiment of the present invention, an example of which is illustrated in the accompanying examples.

The object of this invention is to develop a method for preparing pyrazolinylnaphthalic acid derivatives of general formula

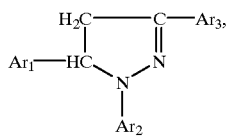

where

Ar$_1$ and Ar$_2$ are unsubstituted or substituted phenyl radicals bearing an alkylated or acylated oxy- or amino group in the para position, or a polynuclear aryl radical; and Ar$_3$ is a substituted N-naphthalimid or 1,8-naphthylene-1',2'-benzimidazole.

The method of the present invention permits, by way of a novel change in the synthetic steps and conditions and simplification of the synthesis, reducing its labor requirements, and enhancing the final product yield and quality (purity grade).

This object is attained by the following. The previously known method includes the reaction of 4-acetylnaphthalic anhydride with organic reagents by way of a series of successive transformations resulting in formation of the corresponding ketone, treating of the latter with phenyl hydrazine or substituted phenyl hydrazine under heating in a solvent, and separation of the final product by filtration.

According to the present invention, the initial 4-acetylnaphthalic anhydride is first reacted with the corresponding aromatic or heterocyclic aldehyde in aqueous alkali medium, the formed disodium salt of cinnamoylnaphthalic acid is condensed with a substituted or unsubstituted aromatic amine obtaining the corresponding ketone and then with phenyl hydrazine, and the formed final product is separated.

The novel modification of the process and the modified stages and synthesis conditions, namely, reacting 4-acetylnaphthalic anhydride not with aromatic amine but with aromatic aldehyde makes it possible to exclude from the process the unsubstituted naphthalic acid comprised in the anhydride in considerable amounts as an impurity. Under the newly developed reaction mode, the unsubstituted acid does not interact chemically with the aromatic aldehyde (in contrast to the amine in the previously known method) and is removed from the reaction mixture as a solution of its sodium salt in the course of filtration of the formed disodium cinnamoyl naphthoate that is essentially insoluble in the aqueous alkali reaction medium.

In this reaction, a considerable amount of by-products are eliminated at the consecutive condensation of cinnamoylnaphhalic acid with aromatic amine. Moreover, the disodium cinamoyl naphthoate is the common intermediate in the synthesis of red range luminophors. For example, its interaction with aniline gives phenylimide of 4-cinnamoylnaphthalic acid while with o-phenylene diamine, 4(5)-cinnamoyl-1,8-naphthoylene-1',2'-benzimidazole is obtained. This allows one to avoid the synthesis of specific intermediates for each color range, thus simplifying the process substantially.

The method of the present invention is realized according to the following scheme:

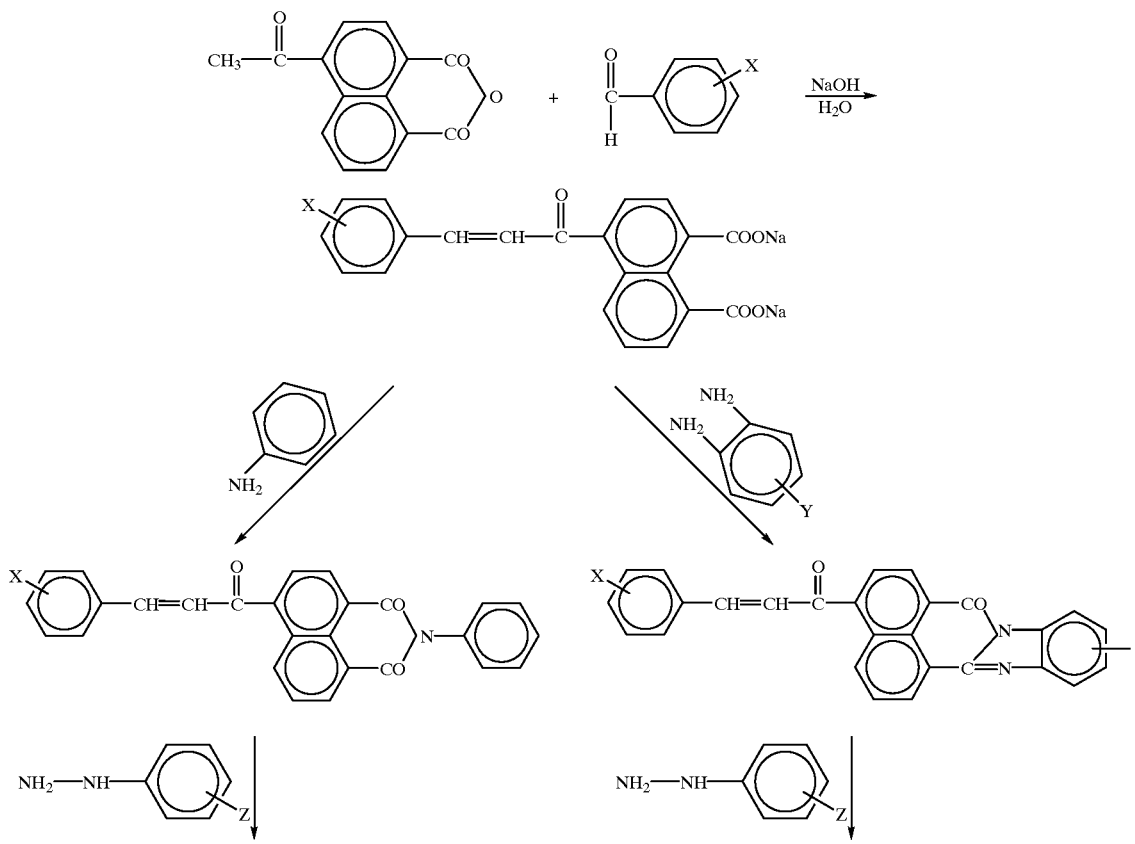

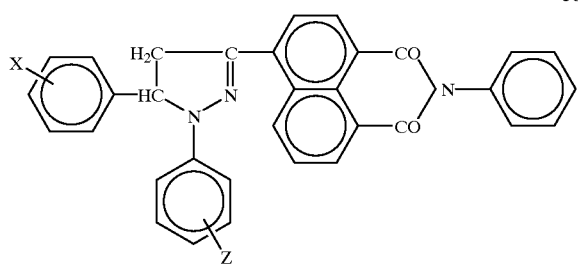 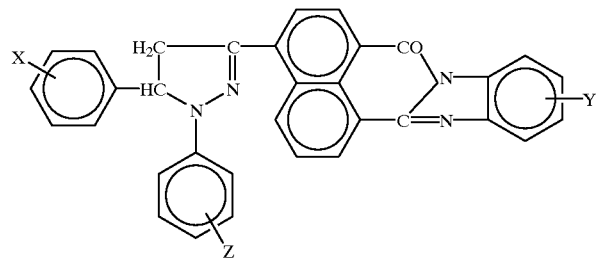

The process stages are as follows:
Treating 4-acetylnaphthalic anhydride with corresponding aldehyde in aqueous alkali medium to obtain disodium salt of 4-cinnamoylnaphthalic acid.
Treating the of 4-cinnamoylnaphthalic acid salt with corresponding mono- or diamine obtaining <<chalcone>>.
Interaction of the obtained <<chalcone>> with phenyl hydrazine or its substituted derivative in a solvent.
Separation of the formed final product from the reaction mixture by filtration.
Purification of the product by chromatography.
Some specific examples of the invention embodiments are presented below.

EXAMPLE 1

Preparation of 4-(1,5-diphenyl-2-pyrazolin-3-yl)-N-phenyl naphthalimide

A mixture of 4-acetylnaphthalic anhydride (10.8 g) (prepared by acenaphthene acylation with acetic anhydride in the presence of anhydrous zinc chloride with the consecutive oxidation of the formed acetyl acenaphthene with sodium dichromate), benzaldehyde (5.25 g), and 4.4% sodium hydroxide solution (120 ml) is stirred for 4 h at room temperature. The precipitate of disodium 4-cinnamoyl naphthoate is separated by filtration and washed with alcohol. A mixture of disodium 4-cinnamoyl naphthoate (15.79 g), aniline (4.89 g), and acetic acid (60 ml) is boiled for 6 h. The reaction mixture is cooled down to room temperature (20° C.). The precipitate is separated by filtration and washed with water and hot alcohol. A mixture of 4-cinnamoyl-N-phenyl naphthalimide (12.1 g), phenyl hydrazine (4.26 g), ethanol (100 ml), and 10% alkali solution (6 ml) is boiled for 6 h, cooled down to 20° C., the precipitate is separated by filtration, washed with water and alcohol, and purified by chromatography on aluminum oxide eluting with chloroform/tetrachloromethane (1:1). The product is obtained as red crystals, m.p. 221–223° C., water-insoluble, soluble in usual organic solvents. Yield: 11.24 g (75%). Luminescence (toluene): $\lambda_{max}$=570 nm.

EXAMPLE 2

Preparation of 4-[(1-phenyl-5-(4-methoxyphenyl)-2-pyrazolin-3-yl]-N-phenyl naphthalimide The compound is prepared and purified as described in Example 1. The initial products: 4-acetylnaphthalic anhydride (10.8 g), anisaldehyde (6.12 g), aniline (4.89 g), and phenyl hydrazine (4.1 g). The product is obtained as dark-red crystals, m.p. 215° C., insoluble in water, soluble in usual organic solvents. Yield: 12.13 g (80%). Luminescence (toluene): $\lambda_{max}$=575 nm.

EXAMPLE 3

Preparation of 4-[(1,5-diphenyl-2-pyrazolin-3-yl)]-N-(4-methoxyphenyl) naphthalimide The compound is prepared and purified as described in Example 1. The initial products: 4-acetylnaphthalic anhydride (21.6 g), benzaldehyde (9.54 g), p-anizidine (13 g), and phenyl hydrazine (10.3 g). The final product yield is 83%. The product is obtained as red crystals, m.p. 268° C., insoluble in water, soluble in usual organic solvents. Luminescence (toluene): $\lambda_{max}$=570 nm.

EXAMPLE 4

Preparation of 4-[1(2-naphthyl)-5-(4-methoxyphenyl)-2-pyrazolin-3-yl]-N-phenyl naphthalimide The compound is prepared and purified as described in Example 1. The initial products: 4-acetylnaphthalic anhydride (10.8 g), anisaldehyde (6.12 g), aniline (4.89 g), and 2-naphthyl phenyl hydrazine (7.48 g). The product is obtained as dark-red crystals, m.p. 202–205° C., insoluble in water, soluble in usual organic solvents. Yield: 15.66 g (75%). Luminescence (toluene): $\lambda_{max}$=617 nm.

EXAMPLE 5

Preparation of 4-[(1-(4-carbomethoxyphenyl)-5-(4-methoxyphenyl-2-pyrazolin-3-yl)]-N-phenyl naphthalimide The compound is prepared and purified as described in Example 1. The initial products: 4-acetylnaphthalic anhydride (10.8 g), anisaldehyde (6.12 g), aniline (4.89 g), and 4-carbomethoxyphenyl hydrazine (7.86 g). The product is obtained as orange crystals, m.p. 255–257° C., water-insoluble, soluble in usual organic solvents. Yield: 17.15 g (81%). Luminescence (toluene): $\lambda_{max}$=570 nm.

EXAMPLE 6

Preparation of 1,5-diphenyl-3-(1,8-naphthoylene-1',2'-benzimidazol-4-yl)-2-pyrazoline The compound is prepared and purified as described in Example 1. The initial products: 4-acetylnaphthalic anhydride (10.8 g), benzaldehyde (5.25 g), o-phenylene diamine (5.68 g), and phenyl hydrazine (4.43 g). The product is obtained as red crystals, m.p. 262–263° C., insoluble in water, soluble in usual organic solvents. Luminescence (toluene): $\lambda_{max}$=598 nm.

EXAMPLE 7

Preparation of 1-phenyl-5-(4-methoxyphenyl)-3-(1,8-naphthoylene-1',2'-benzimidazol-4-yl)-2-pyrazoline The compound is prepared and purified as described in Example 1. The initial products: 4-acetylnaphthalic anhydride (10.8 g), anisaldehyde (6.12 g), o-phenylene diamine (5.68 g), and phenyl hydrazine (4.6 g). The final product yield from 14.1 g of corresponding unsaturated ketone: 13.98 g (82%). The product is obtained as red crystals, m.p. 242–243° C., insoluble in water, soluble in usual organic solvents. Luminescence (toluene): $\lambda_{max}$=600 nm.

EXAMPLE 8

Preparation of 1-phenyl-5-furyl-3-(1,8-naphthoylene-1',2'-benzimidazol-4-yl)-2-pyrazoline The compound is prepared and purified as described in Example 1. The initial products: 4-acetylnaphthalic anhydride (10.8 g), furfan-2-aldehyde (5.25 g), o-phenylene diamine (5.68 g), and phenyl hydrazine (4.4 g). The product is obtained as dark-brown crystals, m.p. 251–252° C., insoluble in water, soluble in usual organic solvents. Yield: 10.35 g (75%). Luminescence (toluene): $\lambda_{max}$=595 nm.

EXAMPLE 9

Preparation of 1-phenyl-5-(4-dimethylaininophenyl)-3-(1,8-naphthoylene-1',2'-benzimidazol-4-yl)-2-pyrazoline The compound is prepared and purified as described in Example 1. The initial products: 4-acetylnaphthalic anhydride (10.8 g), 4-dimethylaminobenzaldehyde (5.25 g), o-phenylene diamine (5 g), and phenyl hydrazine (3.78 g). The final product yield from 11.95 g of corresponding unsaturated compound: 11.5 g (80%).The product is obtained as red crystals, m.p. 256–258° C., insoluble in water, soluble in usual organic solvents. Luminescence (toluene): $\lambda_{max}$=610 nm.

EXAMPLE 10

Preparation of 1-phenyl-5-(4-methoxyphenyl)-3-(1,8-naphthoylene-1',2'-benzimidazol-4-yl)-2-pyrazoline The compound is prepared and purified as described in Example 1. The initial products: 4-acetylnaphthalic anhydride (10.8 g), anisaldehyde (6.12 g), o-naphthylene diamine (8.31 g), and phenyl hydrazine (4.54 g). The product is obtained as red crystals, m.p. 238–240° C., insoluble in water,, soluble in usual organic solvents. Yield: 14.4 g (78%). Luminescence (toluene): $\lambda_{max}$=604 nm.

It is seen from the description and the examples that the method of the present invention develops a novel technologic method for preparing pyrazolinylnaphthalic acid being orange, orange-red, and red range luminophors. The method is simplified and more convenient as compared to known methods due to that, first, disodium salt of cinnamoylnaphthalic acid is a common intermediate in the synthesis of luminophors having all necessary emission colors, so there is no need for preparation of acetyl derivative specific for each color range and, second, there is no need for intermediates purification at each synthesis stage. This reduces considerably the production cost and labor consumption.

Due to the improvements mentioned above, the final product is essentially free of impurities, thus, its quality is improved. Since the losses at the intermediate process stages are reduced (due to the chromatographic purification is unnecessary), the yield of final pure products is enhanced up to 80% in contrast to 50% according to previously known methods. At present, the semi-industrial scale technology has been developed for preparing of products with various emission colors.

It will be apparent to those skilled in the art that various modifications and variations can be made in the construction, configuration, and/or operation of the present invention without departing from the scope or spirit of the invention. For example, in the embodiments mentioned above, various changes may be made to the synthesis or reagents without departing from the scope and spirit of the invention. Further, it may be appropriate to make additional modifications or changes to the reaction conditions without departing from the scope of the invention. Thus, it is intended that the present invention cover the modifications and variations of the invention provided they come within the scope of the appended claims and their equivalents.

We claim:
1. A method for preparing a compound of formula I

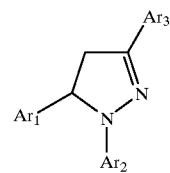

(I)

wherein $Ar_1$ and $Ar_2$ are each independently selected from the group consisting of an unsubstituted phenyl radical, a phenyl radical substituted at the para position with an alkoxy group, an acyloxy group, an alkylamino group or an acylamino group, a naphthyl radical and a polynuclear aromatic radical; and $Ar_3$ is selected from the group consisting of

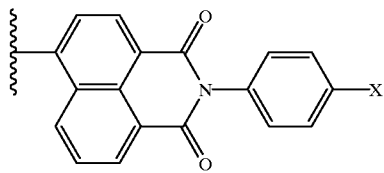

and

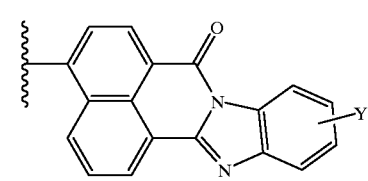

wherein X and Y are each independently selected from the group consisting of hydrogen, an alkoxy group, an acyloxy group, an alkylamino group and an acylamino group; said method comprising the steps of:

(a) reacting 4-acetylnaphthalic anhydride (II)

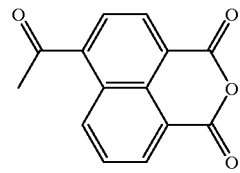

(II)

with an aldehyde of formula III

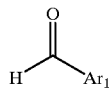
(III)

in the presence of an aqueous base to form a compound of formula IV:

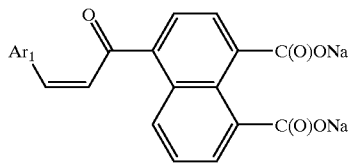
(IV)

(b) boiling the compound of formula IV in the presence of either a compound of formula V:

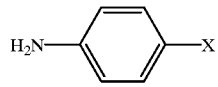
(V)

or a compound of formula VI:

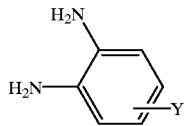
(VI)

to form a compound of formula VII:

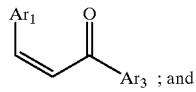
(VII)

(c) boiling the compound of formula VII in the presence of a compound of formula VIII:

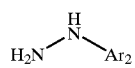
(VIII)

in the presence of ethanol in a 10% alkali solution.

2. A method for preparing a compound of formula I

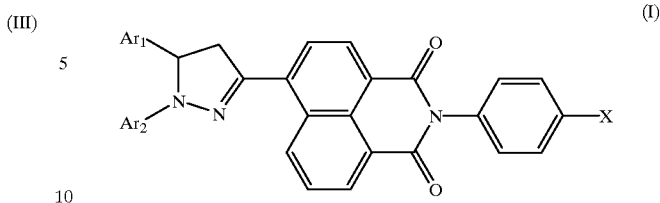
(I)

wherein $Ar_1$ and $Ar_2$ are each independently selected from the group consisting of an unsubstituted phenyl radical, a phenyl radical substituted at the para position with an alkoxy group, an acyloxy group, an alkylamino group or an acylamino group, a naphthyl radical and a polynuclear aromatic radical, and X is selected from the group consisting of hydrogen, an alkoxy group, an acyloxy group, an alkylamino group and an acylamino group;

said method comprising the steps of:

(a) reacting 4-acetylnaphthalic anhydride (II)

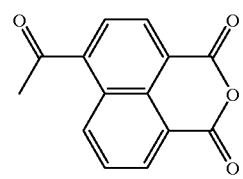
(II)

with an aldehyde of formula III

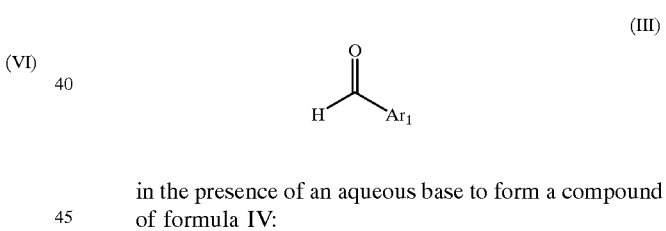
(III)

in the presence of an aqueous base to form a compound of formula IV:

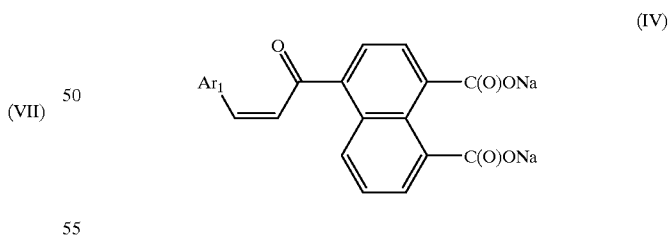
(IV)

(b) boiling the compound of formula IV in the presence of a compound of formula V:

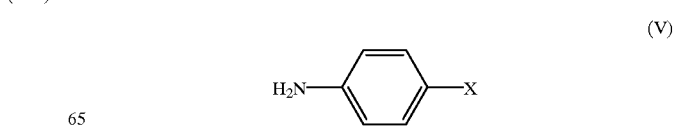
(V)

to form a compound of formula VI:

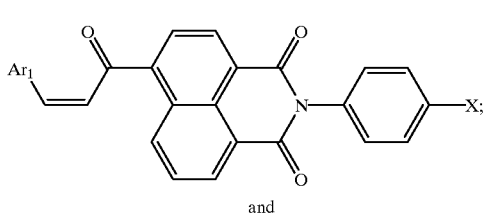

(c) boiling the compound of formula VI in the presence of a compound of formula VII:

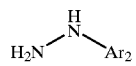

in the presence of ethanol in a 10% alkali solution.

3. A method for preparing a compound of formula I

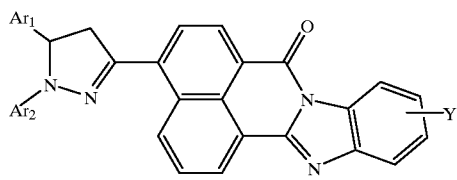

wherein $Ar_1$ and $Ar_2$ are each independently selected from the group consisting of an unsubstituted phenyl radical, a phenyl radical substituted at the para position with an alkoxy group, an acyloxy group, an alkylamino group or an acylamino group, a naphthyl radical and a polynuclear aromatic radical, and Y is selected from the group consisting of hydrogen, an alkoxy group, an acyloxy group, an alkylamino group and an acylamino group;

said method comprising the steps of:

(a) reacting 4-acetylnaphthalic anhydride (II)

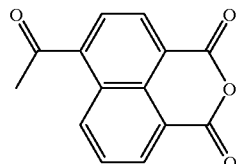

with an aldehyde of formula III

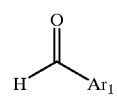

in the presence of an aqueous base to form a compound of formula IV:

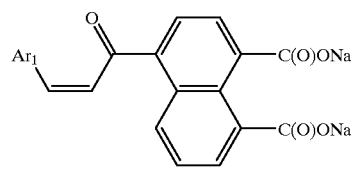

(b) boiling the compound of formula IV in the presence of a compound of formula V:

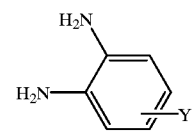

to form a compound of formula VI:

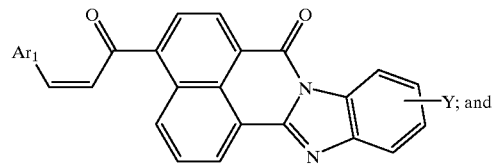

(c) boiling the compound of formula VI in the presence of a compound of formula VII:

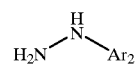

in the presence of ethanol in a 10% alkali solution.

4. The method of claim 1, wherein $Ar_3$ is:

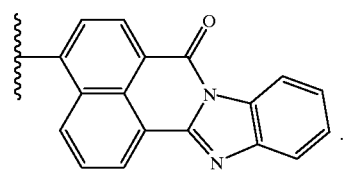

5. The method of claim 3, wherein Y is hydrogen.

6. The method of claim 1, wherein $Ar_3$ is:

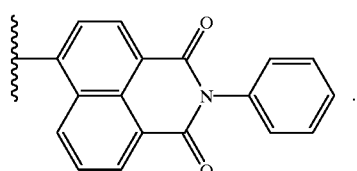

7. The method of claim 2, wherein X is hydrogen.

8. The method of claim 1, wherein Ar$_3$ is:

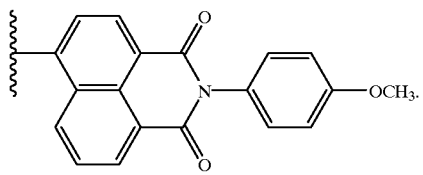

9. The method of claim 2, wherein X is a methoxy group.

10. The method of claim 1, wherein Ar$_1$ and Ar$_2$ are each

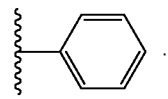

11. The method of claim 2, wherein Ar$_1$ and Ar$_2$ are each

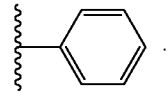

12. The method of claim 3, wherein Ar$_1$ and Ar$_2$ are each

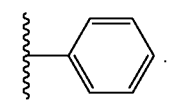

13. The method of claim 1, wherein Ar$_1$ is

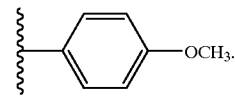

14. The method of claim 2, wherein Ar$_1$ is

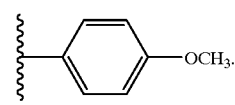

15. The method of claim 3, wherein Ar$_1$ is

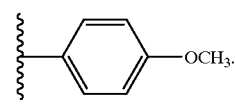

16. The method of claim 1, wherein Ar$_2$ is

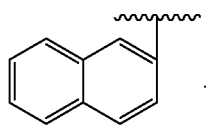

17. The method of claim 2, wherein Ar$_2$ is

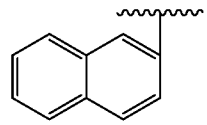

18. The method of claim 1, wherein Ar$_2$ is

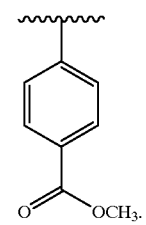

19. The method of claim 2, wherein Ar$_2$ is

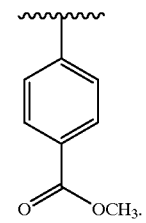

20. The method of claim 1, wherein Ar$_1$ is

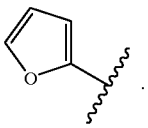

21. The method of claim 3, wherein Ar$_1$ is

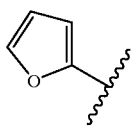

22. The method of claim 1, wherein Ar$_1$ is

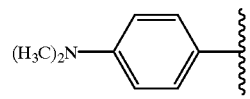

23. The method of claim 3, wherein Ar$_1$ is

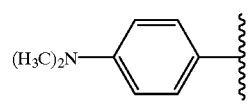

24. The method of claim 1, wherein said 4-acetylnaphthalic anhydride is reacted with said aldehyde of formula III for about 4 hours.

25. The method of claim 2, wherein said 4-acetylnaphthalic anhydride is reacted with said aldehyde of formula III for about 4 hours.

26. The method of claim 3, wherein said 4-acetylnaphthalic anhydride is reacted with said aldehyde of formula III for about 4 hours.

27. The method of claim 1, wherein said compound of formula IV is boiled in the presence of either said compound of formula V or said compound of formula VI for about 6 hours.

28. The method of claim 2, wherein said compound of formula IV is boiled in the presence of said compound of formula V for about 6 hours.

29. The method of claim 3, wherein said compound of formula IV is boiled in the presence of said compound of formula V for about 6 hours.

30. The method of claim 1, wherein said compound of formula VII is boiled in the presence of said compound of formula VIII for about 6 hours.

31. The method of claim 2, wherein said compound of formula VI is boiled in the presence of said compound of formula VII for about 6 hours.

32. The method of claim 3, wherein said compound of formula VI is boiled in the presence of said compound of formula VII for about 6 hours.

33. The method of claim 1, wherein said aqueous base in step (a) is sodium hydroxide.

34. The method of claim 2, wherein said aqueous base in step (a) is sodium hydroxide.

35. The method of claim 3, wherein said aqueous base in step (a) is sodium hydroxide.

36. A method for preparing the compound of formula I (I)

said method comprising the steps of:
(a) reacting 4-acetylnaphthalic anhydride (II)

(II)

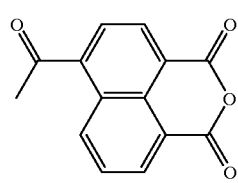

with benzaldehyde (III)

(III)

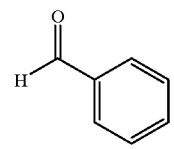

in the presence of aqueous sodium hydroxide to form 4-cinnamoyl naphthoate (IV):

(IV)

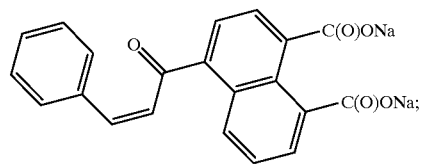

(b) boiling 4-cinnamoyl naphthoate (IV) in the presence of aniline (V):

(V)

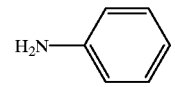

to form the compound of formula VI:

(VI)

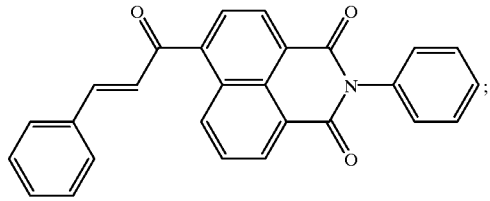

and (c) boiling the compound of formula VI in the presence of phenylhydrazine (VII)

(VII)

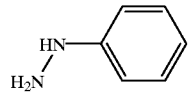

in the presence of ethanol in a 10% alkali solution.

37. A method for preparing the compound of formula I (I)

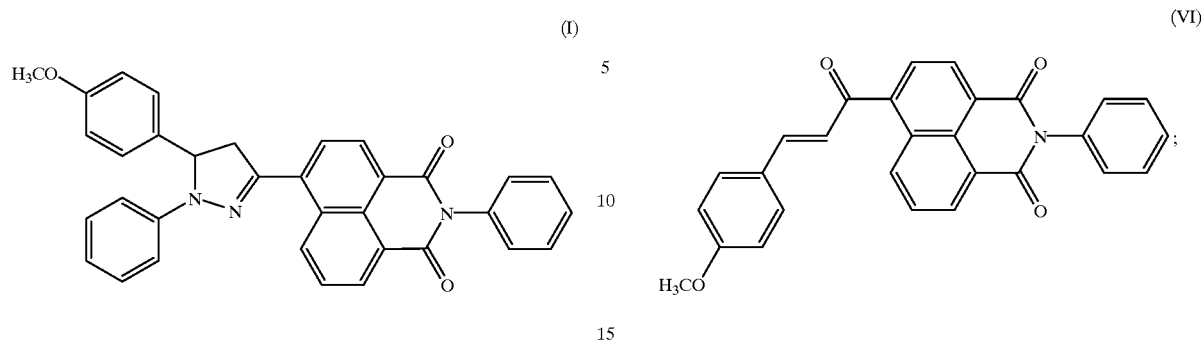

said method comprising the steps of:

(a) reacting 4-acetylnaphthalic anhydride (II)

(VII)

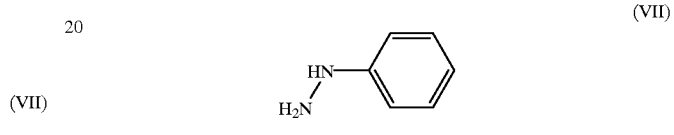

with anisaldehyde (III)

(III)

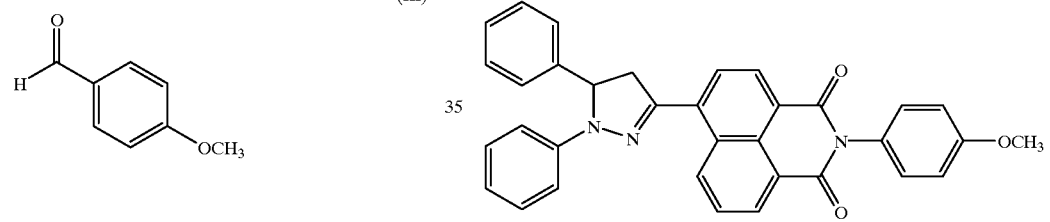

in the presence of aqueous sodium hydroxide to form the compound of formula IV:

(IV)

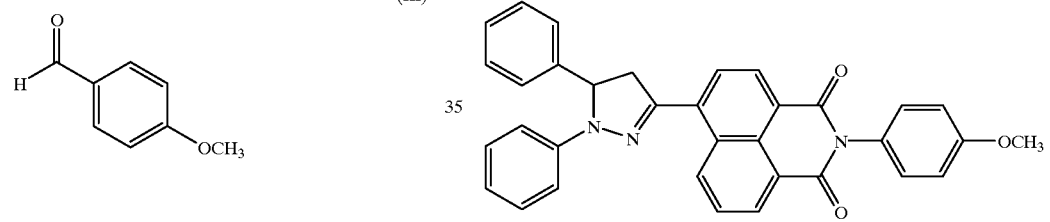

(b) boiling the compound of formula IV in the presence of aniline (V):

(V)

to form the compound of formula VI:

(VI)

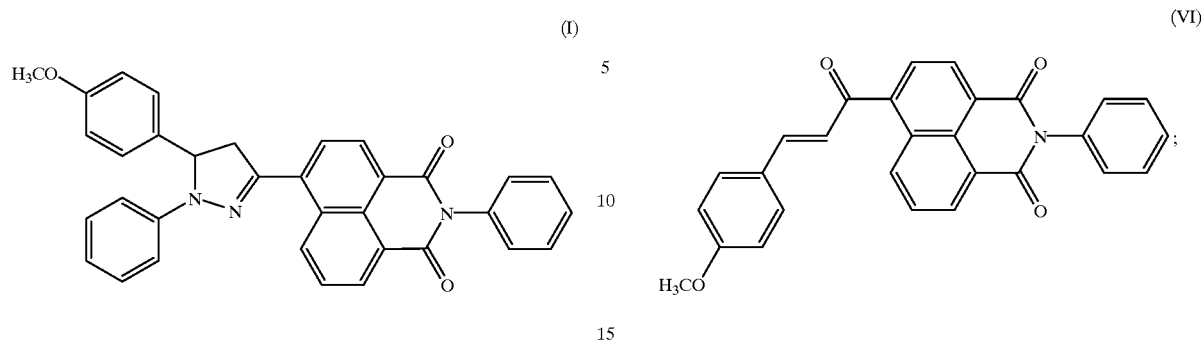

(c) boiling the compound of formula VI in the presence of phenylhydrazine (VII)

(VII)

in the presence of ethanol in a 10% alkali solution.

38. A method for preparing the compound of formula I (I)

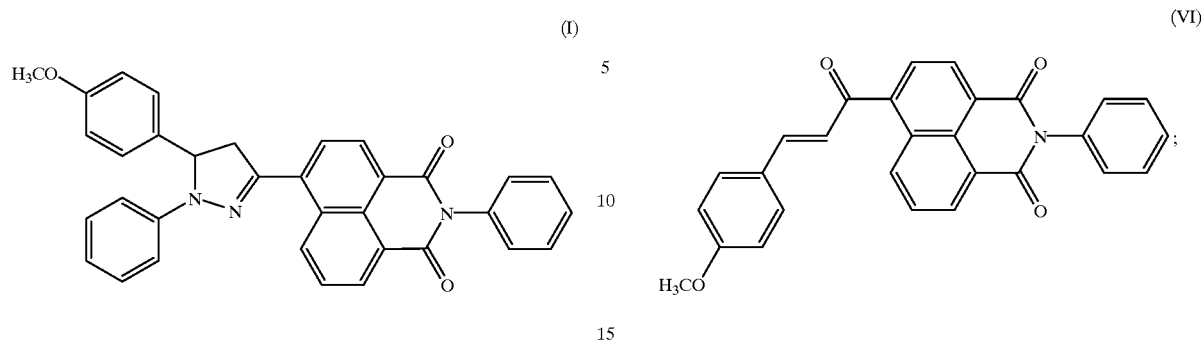

said method comprising the steps of:

(a) reacting 4-acetylnaphthalic anhydride (II)

(VII)

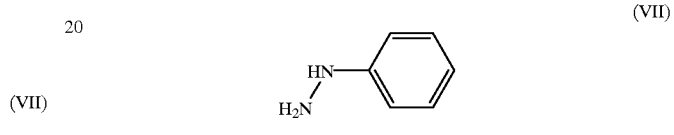

with benzaldehyde (III)

(III)

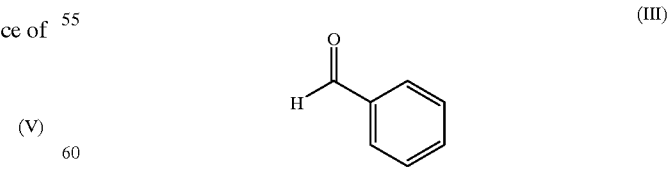

in the presence of aqueous sodium hydroxide to form the compound of formula IV:

(a) reacting 4-acetylnaphthalic anhydride (II)

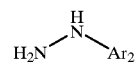

(VII)

with anisaldehyde (III)

(III)

in the presence of aqueous sodium hydroxide to form the compound of formula IV:

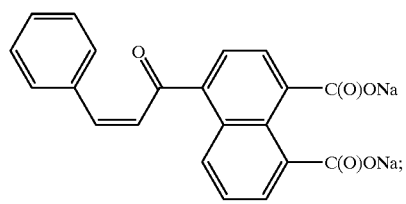

(IV)

(b) boiling the compound of formula IV in the presence of p-anidizine (V):

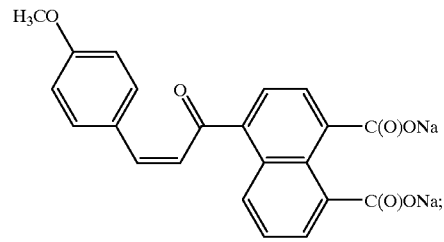

(V)

to form the compound of formula VI:

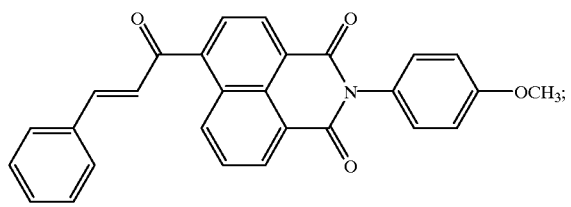

(VI)

(c) boiling the compound of formula VI in the presence of phenylhydrazine (VII)

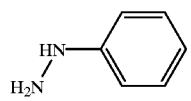

(VII)

in the presence of ethanol in a 10% alkali solution.

39. A method for preparing the compound of formula I (I)

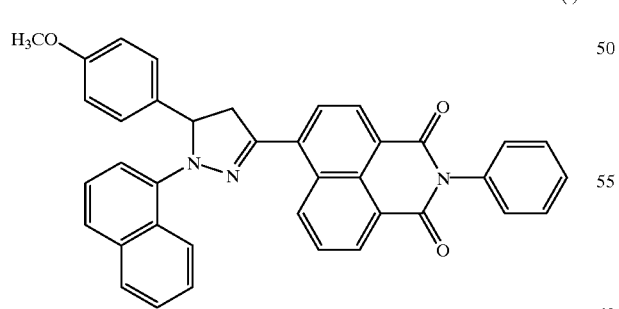

said method comprising the steps of:

(b) boiling the compound of formula IV in the presence of aniline (V):

(V)

to form the compound of formula VI:

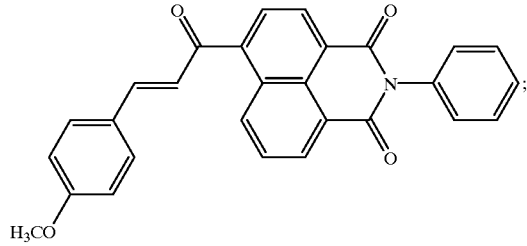

(VI)

and (c) boiling the compound of formula VI in the presence of 2-naphthylphenylhydrazine (VII)

(VII)

[Structure: 2-naphthyl hydrazine, HN-NH₂ on naphthalene]

in the presence of ethanol in a 10% alkali solution.

40. A method for preparing the compound of formula I (I)

[Structure of compound I with H₃CO-phenyl, pyrazoline, naphthalimide with N-phenyl, and OCH₃ ester group]

said method comprising the steps of:

(a) reacting 4-acetylnaphthalic anhydride (II)

(VII)

$$H_2N-\overset{H}{N}-Ar_2$$

with anisaldehyde (III)

(III)

[Structure: 4-methoxybenzaldehyde]

in the presence of aqueous sodium hydroxide to form the compound of formula IV:

(IV)

[Structure: H₃CO-phenyl-CH=CH-C(O)- attached to naphthalene with two C(O)ONa groups]

(b) boiling the compound of formula IV in the presence of aniline (V):

(V)

[Structure: aniline H₂N-C₆H₅]

to form the compound of formula VI:

(VI)

[Structure of compound VI: H₃CO-phenyl-CH=CH-C(O)- attached to naphthalimide with N-phenyl]

and (c) boiling the compound of formula VI in the presence of 4-carbomethoxyphenylhydrazine (VII)

(VII)

[Structure: 4-carbomethoxyphenylhydrazine HN(NH₂)-C₆H₄-C(O)OCH₃]

in the presence of ethanol in a 10% alkali solution.

41. A method for preparing the compound of formula I (I)

[Structure of compound I: diphenyl pyrazoline fused with naphtho-benzimidazole system]

said method comprising the steps of:

(a) reacting 4-acetylnaphthalic anhydride (II)

(VII)

$$H_2N-\overset{H}{N}-Ar_2$$

with benzaldehyde (III)

(III)

[Structure: benzaldehyde]

in the presence of aqueous sodium hydroxide to form the compound of formula IV:

(IV)

[structure: chalcone-naphthalene with two C(O)ONa groups]

(b) boiling the compound of formula IV in the presence of o-phenylene diamine (V):

(V)

[structure: o-phenylenediamine]

to form the compound of formula VI:

(VI)

[structure: benzimidazole-fused naphthalimide with chalcone]

and (c) boiling the compound of formula VI in the presence of phenylhydrazine (VII):

(VII)

[structure: phenylhydrazine]

in the presence of ethanol in a 10% alkali solution.

42. A method for preparing the compound of formula I (I)

[structure: pyrazoline-containing compound with methoxyphenyl and benzimidazole-naphthalimide]

said method comprising the steps of:

(a) reacting 4-acetylnaphthalic anhydride (II)

(VII)

[structure: H₂N-NH-Ar₂]

with anisaldehyde (III)

(III)

[structure: 4-methoxybenzaldehyde]

in the presence of aqueous sodium hydroxide to form the compound of formula IV:

(IV)

[structure: methoxy-chalcone-naphthalene with two C(O)ONa groups]

(b) boiling the compound of formula IV in the presence of o-phenylene diamine (V):

(V)

[structure: o-phenylenediamine]

to form the compound of formula VI:

(VI)

[structure: methoxy-chalcone benzimidazole-fused naphthalimide]

and (c) boiling the compound of formula VI in the presence of phenyl hydrazine (VIl):

(VII)

[structure: phenylhydrazine]

in the presence of ethanol in a 10% alkali solution.

43. A method for preparing the compound of formula I (I)

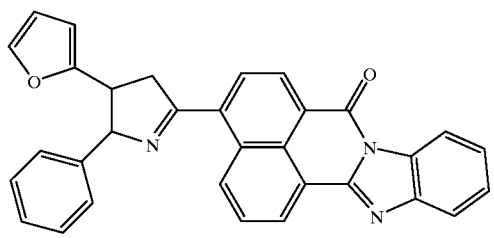

said method comprising the steps of:
(a) reacting 4-acetylnaphthalic anhydride (II)

(VII)

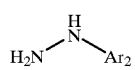

with furan-2-aldehyde (III)

(III)

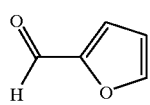

in the presence of aqueous sodium hydroxide to form the compound of formula IV:

(IV)

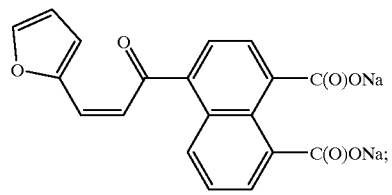

(b) boiling the compound of formula IV in the presence of o-phenylene diamine (V):

(V)

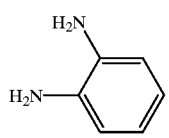

to form the compound of formula VI:

(VI)

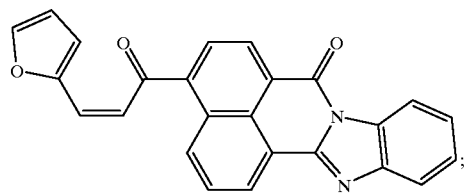

and (c) boiling the compound of formula VI in the presence of phenylhydrazine (VII):

(VII)

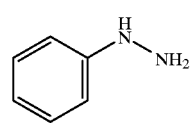

in the presence of ethanol in a 10% alkali solution.

44. A method for preparing the compound of formula I (I)

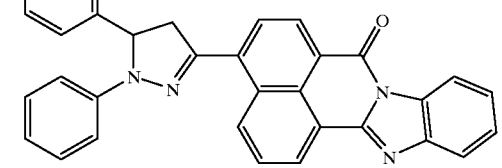

said method comprising the steps of:

(a) reacting 4-acetylnaphthalic anhydride (II)

(VII)

with 4-N,N-dimethylaminobenzaldehyde (III)

(III)

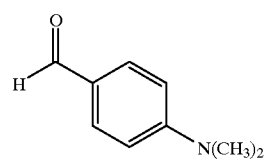

in the presence of aqueous sodium hydroxide to form the compound of formula IV:

(IV)

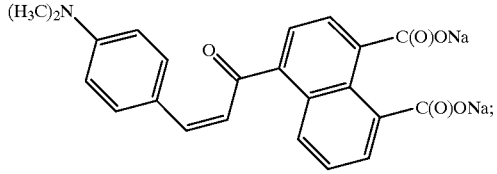

(b) boiling the compound of formula IV in the presence of o-phenylene diamine (V):

with anisaldehyde (III)

(III)

(structure: 4-methoxybenzaldehyde)

in the presence of aqueous sodium hydroxide to form the compound of formula IV:

(IV)

(structure of formula IV)

(b) boiling the compound of formula IV in the presence of o-phenylene diamine (V):

(V)

(structure: o-phenylenediamine)

to form the compound of formula VI:

(VI)

(structure of formula VI)

and (c) boiling the compound of formula VI in the presence of phenylhydrazine (VII):

(VII)

(structure: phenylhydrazine)

in the presence of ethanol in a 10% alkali solution.

(V)

(structure: o-phenylenediamine)

to form the compound of formula VI:

(VI)

(structure of formula VI)

and (c) boiling the compound of formula VI in the presence of phenylhydrazine (VII):

(VII)

(structure: phenylhydrazine)

in the presence of ethanol in a 10% alkali solution.

45. A method for preparing the compound of formula I (I)

(structure of formula I)

said method comprising the steps of:

(a) reacting 4-acetylnaphthalic anhydride (II)

(VII)

(structure: $H_2N-NH-Ar_2$)

* * * * *